United States Patent
Lavrentiev et al.

(10) Patent No.: US 8,233,075 B2
(45) Date of Patent: Jul. 31, 2012

(54) USER-AIDED AUTO-FOCUS

(75) Inventors: Michael Lavrentiev, Haifa (IL); Stuart Wolf, Yokneam (IL); Doron Adler, Nesher (IL); Albert M. Juergens, III, Boylston, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 751 days.

(21) Appl. No.: 12/125,832

(22) Filed: May 22, 2008

(65) Prior Publication Data

US 2009/0046196 A1   Feb. 19, 2009

Related U.S. Application Data

(60) Provisional application No. 60/940,047, filed on May 24, 2007.

(51) Int. Cl.
   G03B 13/00 (2006.01)
   H04N 5/232 (2006.01)
   A61B 1/06 (2006.01)
(52) U.S. Cl. ......... 348/345; 348/353; 348/354; 600/167
(58) Field of Classification Search ................. 348/345, 348/346, 349, 353–356; 600/167; 396/77, 396/131
   See application file for complete search history.

(56) References Cited

U.S. PATENT DOCUMENTS

| | | | |
|---|---|---|---|
| 4,389,565 A | 6/1983 | Numata | |
| 5,589,874 A | 12/1996 | Buchin | |
| 6,749,561 B2 | 6/2004 | Kazakevich | |
| 7,453,490 B2 | 11/2008 | Gunday | |
| 2001/0048479 A1* | 12/2001 | Ohkawara et al. | 348/360 |
| 2002/0039242 A1 | 4/2002 | Sasaki et al. | |
| 2005/0018066 A1* | 1/2005 | Hofer | 348/333.02 |
| 2006/0001764 A1* | 1/2006 | Stavely et al. | 348/362 |
| 2006/0133791 A1* | 6/2006 | Miyata | 396/103 |
| 2007/0203394 A1* | 8/2007 | Wiklof | 600/109 |

FOREIGN PATENT DOCUMENTS

| | | |
|---|---|---|
| EP | 0451865 B1 | 6/1996 |
| JP | Sho 60-050506 | 3/1985 |
| JP | Sho 62-123416 | 6/1987 |
| JP | 63-281576 A | 11/1988 |
| JP | Hei 02-276364 | 11/1990 |

(Continued)

OTHER PUBLICATIONS

Office Action from the Patent Office of Japan dated Dec. 8, 2009 for corresponding Japanese patent application No. 2008-136208, (with English summary) 5 pages.

(Continued)

*Primary Examiner* — David Ometz
*Assistant Examiner* — Dillon Durnford Geszvain
(74) *Attorney, Agent, or Firm* — Ganz Law, P.C.

(57) ABSTRACT

Methods and systems for adjusting a video imaging system that includes an auto-focus mechanism wherein an input from a user of the video imaging system invokes an auto-focus procedure. Responsive to the input, the auto-focus mechanism is scanned over a range of focal distance from a first setting to a second setting indicated by the input. A sequence of images using the video imaging system is captured while scanning the auto-focus mechanism over the range. The images in the sequence are processed so as to compute a measure of focal quality with respect to each of the images. The measure of the focal quality is analyzed so as to select an optimal focal distance, and the auto-focus mechanism is set to the selected focal distance.

22 Claims, 5 Drawing Sheets

FOREIGN PATENT DOCUMENTS

| | | |
|---|---|---|
| JP | 4-37827 | 2/1992 |
| JP | Hei 05-056328 | 3/1993 |
| JP | Hei 06-178188 | 6/1994 |
| JP | 11-103408 | 4/1999 |
| JP | 2000-338387 A | 12/2000 |
| JP | 2002-318341 A | 10/2002 |
| JP | 2003-241066 | 8/2003 |
| JP | 2004-061942 | 2/2004 |
| JP | 2004-294788 | 10/2004 |
| JP | 2004-361484 | 12/2004 |
| JP | 2005-202064 | 7/2005 |
| JP | 2006-171588 | 6/2006 |
| JP | 2006-243373 | 9/2006 |
| JP | 2007-094023 | 12/2007 |

OTHER PUBLICATIONS

Office Action dated Feb. 22, 2011, and issued by the Patent Office of Japan in Japanese Patent Application No. 2008-136208; 2 pages.

Office Action, dated Jul. 26, 2011, issued by the Japan Patent and Trademark Office for Japanese Patent Application No. 2008-136208 (in Japanese language); 3 pages. Informal English language translation included; 1 page.

Office Action dated Apr. 12, 2011, and issued by the German Patent and Trademark Office in German Patent Application No. 10 2008 024 851.7 (in the German language); 10 pages—English language translation of Office Action included—11 pages.

\* cited by examiner

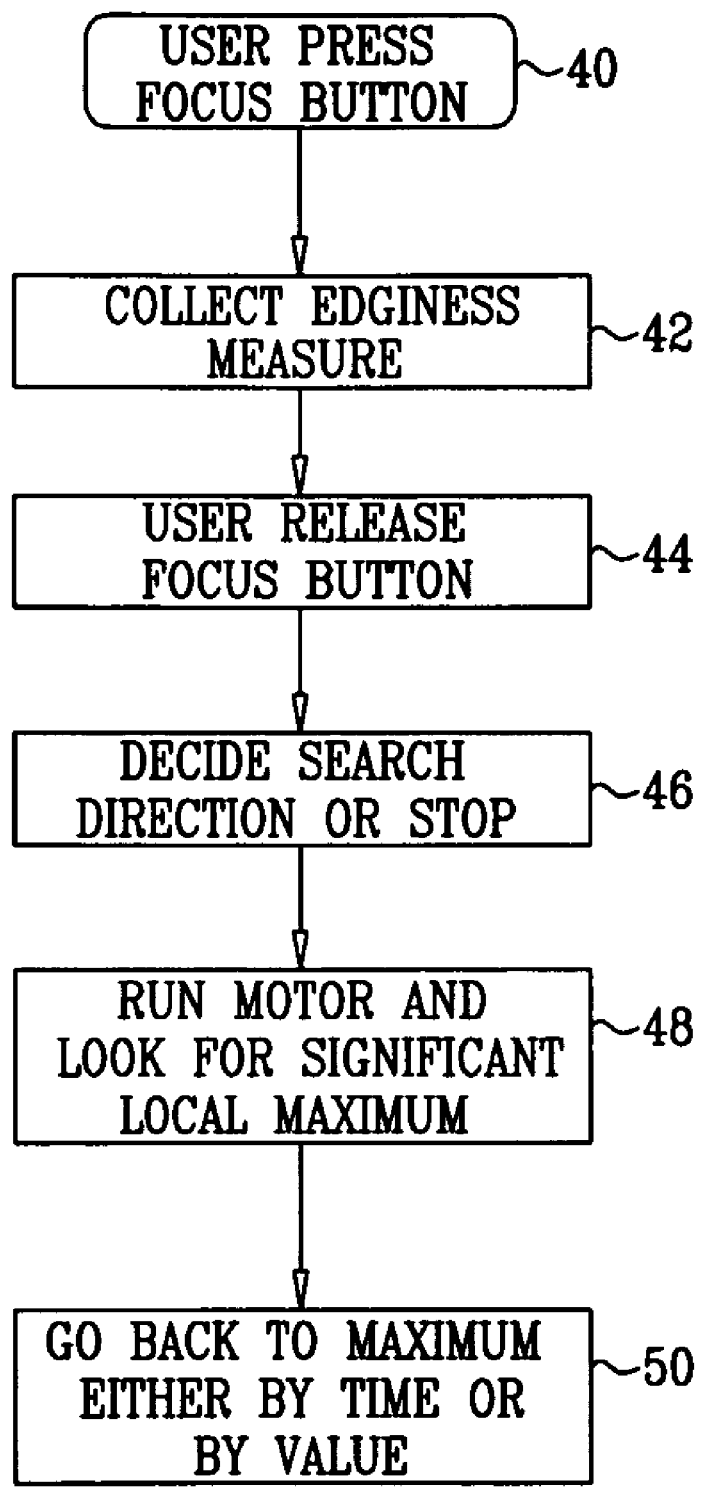

USER-AIDED AUTO-FOCUS

RELATED APPLICATIONS

This application claims the benefit of and priority to U.S. Provisional Application Ser. No. 60/940,047, filed May 24, 2007 the contents of which are hereby incorporated by reference as if recited in full herein for all purposes.

BACKGROUND

This application relates generally to electronic imaging, and is particularly suited for automatic focusing of electronic, medical imaging devices.

Endoscopic cameras are used, in conjunction with suitable endoscopic optics, to capture and display images of structures within the body of a subject. Such cameras commonly incorporate auto-focus mechanisms, which automatically focus the optics in order to optimize the quality of the captured image.

Various types of auto-focus mechanisms are known in the art of endoscopic imaging. For example, U.S. Pat. No. 4,389,565, whose disclosure is incorporated herein by reference, describes an automatic focusing device in which the focus of an image of the object to be observed is automatically controlled based on the distance to the object. The distance is automatically detected by varying the intensity of the light source that is used to illuminate the object and measuring the intensity of the light reflected by the object. According to the distance, a focusing lens is driven to obtain a focused image.

As another example, U.S. Pat. No. 6,749,561, whose disclosure is incorporated herein by reference, describes an auto-focusing endoscopic system, which uses a transition between an imaging area and a non-imaging area in the endoscopic image in focusing the endoscopic optics. This approach is said to allow for robust auto-focusing operation regardless of contrast characteristics of the environment.

Prior art auto-focus mechanisms systems typically set the focal distance of the imaging optics based on measurement and optimization of certain image characteristics. When the characteristics change, the auto-focus mechanism will typically seek a new focus. In some imaging environments, however, it may be difficult to find a clear optimum. As a result, the mechanism may spend a long time in seeking a focus and may then settle at an incorrect focal distance or resume seeking unnecessarily as the image changes. These sorts of problems are common, for example, in some endoscopic applications. Accordingly, there is a need for improved auto-focus methods and systems.

SUMMARY

In the embodiments of the inventive subject matter that are described hereinbelow, auto-focus problems of these sorts are addressed with the aid of the user of the system. Auto-focus operation is invoked in response to an input by the user, which causes the auto-focus mechanism to begin scanning the focal distance of the imaging optics. The mechanism continues scanning from an initial setting of the focal distance up to a second setting, and the system meanwhile captures images and evaluates a measure of their focal quality in order to automatically find the optimal focal distance. Subsequently, the auto-focus mechanism may remain at this optimal focus, without seeking a new focus even when image characteristics change, until the user again actuates the auto-focus control.

In some embodiments, the user may choose the second setting by appropriate operation of the input, and thus controls the range over which the auto-focus mechanism scans in seeking the optimal focus. It is desirable that the user choose the second setting so that the imaging optics at the second setting are adjusted to a focal distance that is approximately optimal. This sort of user input can assist the system in converging rapidly to the proper focal distance.

Although the embodiments described hereinbelow relate specifically to endoscopic imaging, the principles of the inventive subject matter may similarly be applied in providing interactive auto-focus functionality in other electronic imaging applications.

There is therefore provided, in accordance with an embodiment of the inventive subject matter, a method for adjusting a video imaging system that includes an auto-focus mechanism, the method including:

receiving an input from a user of the video imaging system invoking an auto-focus procedure;

responsively to the input, scanning the auto-focus mechanism over a range of focal distance from a first setting to a second setting indicated by the input;

capturing a sequence of images using the video imaging system while scanning the auto-focus mechanism over the range;

processing the images in the sequence so as to compute a measure of focal quality with respect to each of the images;

analyzing the measure of the focal quality so as to select an optimal focal distance; and setting the auto-focus mechanism to the selected focal distance.

There is also provided, in accordance with an embodiment of the inventive subject matter, apparatus for video imaging, including:

an image sensor;

imaging optics, which are configured to form an image on the image sensor and include an auto-focus mechanism for adjusting a focal distance of the imaging optics;

an auto-focus control, which is operable by a user of the apparatus to generate an input invoking an auto-focus procedure; and a controller, which is configured to scan the auto-focus mechanism, responsively to the input, over a range of focal distances from a first setting to a second setting indicated by the input, and to process a sequence of images captured by the image sensor while scanning the auto-focus mechanism over the range so as to compute a measure of focal quality with respect to each of the images, and to analyze the measure of the focal quality so as to select an optimal focal distance and set the auto-focus mechanism to the selected focal distance.

In some embodiments, receiving the input includes sensing actuation and release of a user control associated with the video imaging system. In a disclosed embodiment, the video imaging system includes a camera, and the user control includes a button on the camera. Typically, scanning the auto-focus mechanism includes determining the second setting to be the focal distance at which the user control was released, wherein the release of the user control is indicative of an approximation by the user of the optimal focal distance.

In a disclosed embodiment, processing the images includes computing the measure of focal quality by evaluating edges in the images.

In some embodiments, processing the images includes computing the measure of focal quality over a plurality of windows within each of the images, and analyzing the measure of the focal quality includes selecting at least one of the windows so as to determine the optimal focal distance. Additionally or alternatively, analyzing the measure of focal quality includes evaluating a profile of the measure of focal quality as a function of the focal distance against an expected profile that is associated with optical defocusing.

In some embodiments, scanning the auto-focus mechanism includes scanning the focal distance in a first direction, and the method includes performing at least one scan of the focal distance in a second direction, opposite to the first direction, in order to find the optimal focal distance. In one such embodiment, scanning the focal distance in the first direction includes determining a threshold value of the measure that is indicative of the optimal focal distance while scanning in the first direction, and performing the at least one scan of the focal distance in the second direction includes terminating the at least one scan when the measure passes the threshold or when a predetermined time limit has expired.

In a disclosed embodiment, capturing the sequence of images includes capturing the images of an anatomical structure inside a body of a subject using an endoscope.

Optionally, the input is received while the video imaging system is directed to image a target used in a color balancing procedure.

These and other embodiments are described in more detail in the following detailed descriptions and the figures. The various methods may be implemented as a set of machine readable and executable instructions stored on known storage media for computing devices.

The foregoing is not intended to be an exhaustive list of embodiments and features of the inventive subject matter. Persons skilled in the art are capable of appreciating other embodiments and features from the following detailed description in conjunction with the drawings.

The inventive subject matter will be more fully understood from the following detailed description of the embodiments thereof, taken together with the drawings in which:

BRIEF DESCRIPTION OF THE DRAWINGS

The following figures show embodiments according to the inventive subject matter, unless noted as showing prior art.

FIG. 2 is a flow chart that schematically illustrates a method for user-actuated auto-focus, in accordance with an embodiment of the inventive subject matter;

DETAILED DESCRIPTION

Figure 1:
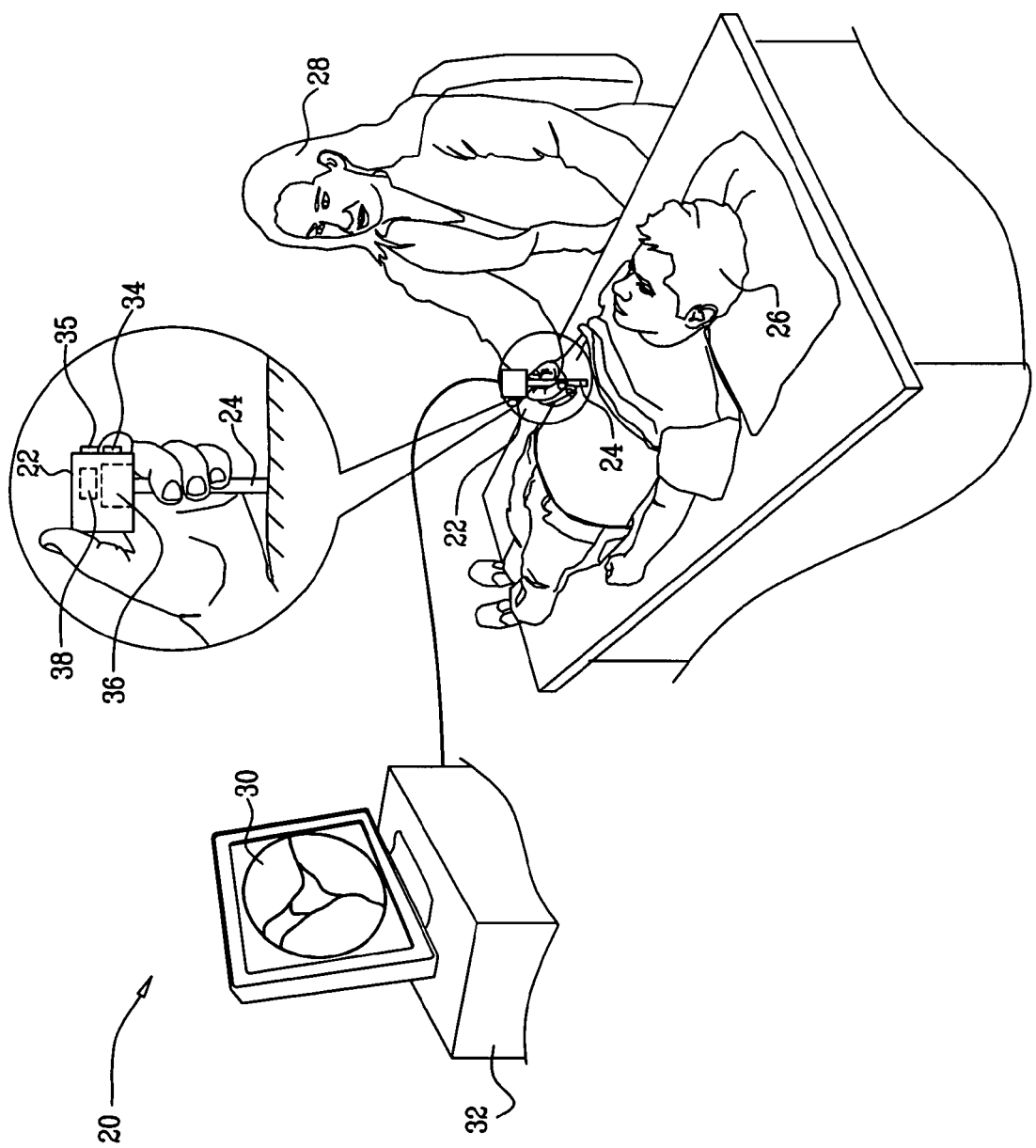
FIG. 1 is a schematic, pictorial illustration of a system for endoscopic imaging with a user-actuated auto-focus mechanism, in accordance with an embodiment of the inventive subject matter.

Representative embodiments according to the inventive subject matter are shown in FIGS. 1-5, wherein the same or generally similar features share common reference numerals.

FIG. 1 is a schematic, pictorial illustration of a system 20 for endoscopic imaging, in accordance with an embodiment of the inventive subject matter. A video camera 22 captures images 30 of anatomical structures within the body of a patient 26 via an endoscope 24. In the example shown in the figure, endoscope 24 is a rigid laparoscope, and camera 22 is coupled to the proximal end of the laparoscope, outside the patient's body. Alternatively, endoscope 24 may comprise a rigid or flexible endoscope of any other suitable type, and the camera may be located at either the proximal or the distal end (assuming the camera is configured to allow automatic focal adjustment). Further alternatively, the principles of the inventive subject matter may be implemented in video imaging systems of other types, such as systems for machine vision and microscopy, and are by no means limited to endoscopic applications.

Camera 22 comprises imaging optics 36, which focus an image onto an image sensor 38. The image sensor may comprise any suitable type of sensing device, such as a CCD or CMOS-type sensor, in either a single-sensor or multi-sensor configuration. Optics 36 are adjustable, under external control, in order to vary the focal distance of the images that are formed on the image sensor. The adjustment may be carried out, for example, by motorized motion of one or more lenses in optics 36, or alternatively using any other suitable method of focal adjustment that is known in the art. A user 28, typically a medical practitioner, aims endoscope 24 so that the sensor captures images of the desired anatomical structures. A console 32 processes the output of sensor 38 in order to produce video images 30 in the appropriate format.

After inserting endoscope 24 into the patient's body and aiming the endoscope toward the anatomical structure of interest, user 28 actuates auto-focus controls 34 and 35. Alternatively, this focusing procedure may be carried out simultaneously with color balancing ("white balance"), while the user aims the endoscope toward a calibration target, such as a white pad (not shown). Controls 34 and 35 may comprise dual push-buttons, as is illustrated in the figure, for toggling the focal mechanism forward and back. Alternatively, system 20 may comprise a single auto-focus control or multiple push-buttons or switches or controls of any other suitable type. Actuation of controls 34 and 35 invokes an auto-focus process, in which optics 36 are set to an optimal focal distance, as described with reference to the figures that follow. This auto-focus process may be carried out under the control of console 32 and/or by another suitable controller (not shown) that is contained within camera 22 or in another housing.

FIG. 2 is a flow chart that schematically illustrates a method for user-actuated auto-focus, in accordance with an embodiment of the inventive subject matter. The method is initiated when user 28 presses auto-focus control 34 or 35, at an actuation step 40. While the user presses the controls, the controller (such as console 32) drives the focal adjustment mechanism of optics 36 so as to gradually scan (increase and/or decrease) the focal distance.

Meanwhile, image sensor 38 captures a succession of images 30, which are typically output for viewing by the user. The controller measures one or more characteristics of the images that are indicative of image focal quality, and records the measurement it has made as a function of focal distance, at an image measurement step 42. For example, the controller may measure image "edginess," i.e., a measure of the sharpness, or contrast, of edges in the image. For this purpose, the controller may digitally filter the image using a suitable kernel, and then sum the resulting output values. One kernel that may be used for this purpose is $$\begin{pmatrix} -1 & 2 & -1 \\ 2 & -4 & 2 \\ -1 & 2 & -1 \end{pmatrix}.$$

Alternatively, the filter may output at each pixel the difference between the maximum and minimum pixel values in a certain neighborhood (such as a 3×3 neighborhood) of the pixel.

Alternatively, the controller may measure any other suitable image characteristic or group of characteristics that are indicative of focal quality.

The user-actuated scan of focal distance terminates when the user releases the auto-focus controls, at a release step 44. (Alternatively, the user may terminate the scan by actuating the controls in a certain way, or by any other suitable action or sequence of actions.) For best results, it is desirable that the user observe images 30 and terminate the scan immediately after reaching the setting at which the perceived image quality is best. In this case, the controller will generally have to perform little or no additional scanning in order to reach the final focal setting, and the likelihood is increased that the scan will result in a setting at which the image features of interest to the user are sharply focused. Alternatively, however, the user may terminate the scan at any other desired point.

At the conclusion of steps 40-44, the controller will have collected measurements of focal quality as a function of focal distance setting over a range of focal distances. The controller evaluates these collected measurements in order to decide what additional, automatic focal adjustment may still be needed, at a decision step 46. If the current setting is the one that gave the optimal (typically maximal) quality measure, the controller stops the auto-focus process and takes no further action.

Otherwise, the controller chooses the direction for adjustment that should, according to the collected measurements, lead to an increase in the focal quality. The controller drives the auto-focus mechanism to adjust the focus of optics 36 in the chosen direction, at an automatic adjustment step 48. The adjustment continues until the controller passes a significant maximum of the focal quality measure. "Significant" in this context means, for example, that the maximal measure exceeds a certain baseline value by a predetermined threshold or percentage. After passing and identifying the maximum, the controller drives the focal adjustment mechanism back to the setting that gave the optimal quality measure, at a concluding step 50. The controller may return to this setting either by tracking the focal quality measure until it returns to the maximal value or by running the adjustment mechanism for the required time or distance to reach the optimal setting.

Figure 3A:
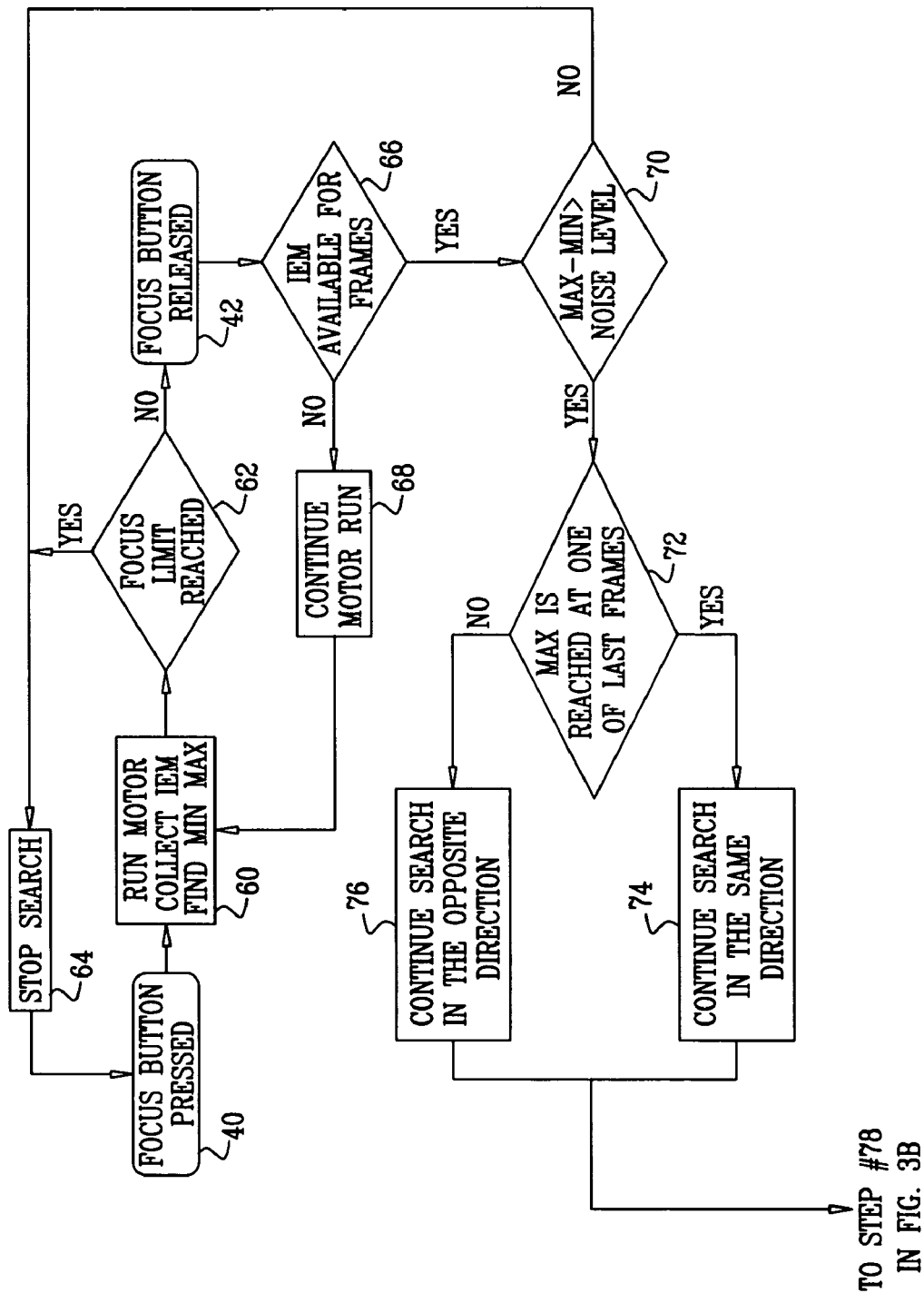
FIGS. 3A and 3B are a flow chart that schematically shows a detailed implementation of the method of FIG. 2, in accordance with an embodiment of the inventive subject matter.
Figure 3B:
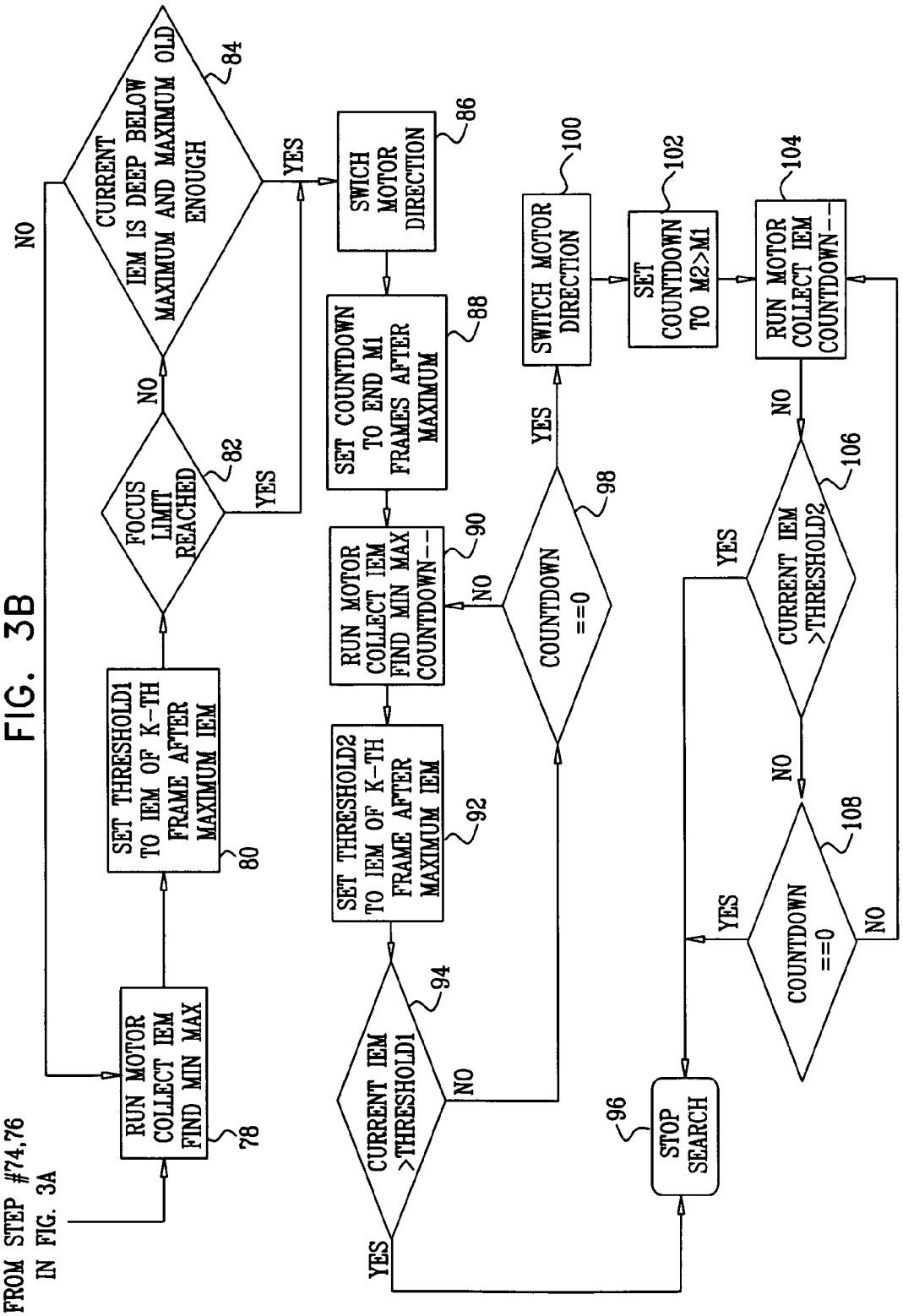

FIGS. 3A and 3B are a flow chart that schematically shows details of an exemplary implementation of the method of FIG. 2, in accordance with an embodiment of the inventive subject matter. As explained above, after the user actuates controls 34 and/or 35 at step 40, the controller runs the auto-focus motor (or other mechanism) and computes an image edginess measure (IEM) as a function of focal setting, at an IEM collection step 60. The controller analyzes the IEM results to find the maximum and baseline values, wherein the baseline may typically be set to the minimum IEM value.

The IEM may be computed over the entire image or, alternatively, over a certain window within the image, such as a selected area in the center of the image. The window size and shape may be adjusted according to the needs of the application. The window may be chosen dynamically from among a number of options in order to give the strongest maximum or best contrast between maximum and baseline, or to give a focal distance (maximum IEM value) that is closest to the setting at which the user subsequently releases controls 34 and 35 at step 44. Additionally or alternatively, the IEM may be computed over each of a number of different windows, and the focal distance may be set on the basis of a combination of IEM values taken from the different windows.

The initial scan of focal distance ends, as noted above, when the user releases controls 34 and 35 at step 42 or, alternatively, if the auto-focus mechanism previously reaches the end of its range, at a range limit step 62. In this latter event, the controller stops the scan at the limit, at a search termination step 64. If the user is satisfied with the end-of-range setting, the user may release the controls, and the process will terminate at this point. Otherwise, the user may actuate the controls once more, thus returning to step 40. The controller will then repeat step 60, this time running the auto-focus mechanism in the opposite direction from the previous scan.

When the user releases the focus controls at step 42, the controller checks whether the duration of step 60 was sufficient to collect IEM data for a certain minimal number of video frames, at an IEM availability checking step 66. Typically, for reliable results, the controller uses data from at least ten frames, for example. If the user released the controls before a sufficient number of frames was collected, the controller may continue to run the auto-focus mechanism and collect IEM data, at a continued running step 68, until it has a sufficient number of frames or until it reaches the focus limit.

In an alternative embodiment, the search may terminate at step 64 if the user has actuated the auto-focus controls for less than the minimal number of frames. This option permits the user to perform manual focus adjustment.

After the focal scan has terminated, having collected a sufficient number of frames, the controller checks whether the scan of focal distance passed through an optimal focal point, at a focus checking step 70. In other words, in the present embodiment, the controller determines whether the scan passed through a significant local maximum. For example, the difference between the maximal and minimal values of the IEM may be compared with an average background level of the images (which may be either a measured value or a predefined level). For example, the background level may be defined as a level of IEM when the image is not in focus or when no edges present. The maximum may be considered significant if the difference between maximal and minimal IEM values exceeds the average background level by a certain factor, such as three. Alternatively or additionally, other conditions may be used in identifying significant maxima, such as the profile of the IEM curve, as explained below in reference to FIG. 5. In any case, if the scan did not pass through a significant maximum, the search terminates at step 64, and the user is prompted to actuate the focus controls once again to resume the search.

If the controller finds a significant maximum at step 70, it determines whether the maximum occurred within the last few frames of the scan, at a maximum identification step 72. If so, the controller continues to run the auto-focus mechanism in the same direction as in the most recent pass through step 60, at a scan continuation step 74. The purpose of this step is to ensure that the frame that was found to have the maximum IEM value is the true focal point, and not an inferior local maximum. Otherwise, if the maximum was passed more than a few frames before the end of the most recent pass through step 60, the controller runs the auto-focus mechanism in the opposite direction, at a scan reversal step 76. Typically, the controller seeks to scan over a sufficient range of frames to have at least ten frames on either side of the frame with the maximum IEM value (assuming that the maximum is not found at or very near the end of the focal range of the auto-focus mechanism).

In either case (step 74 or 76), the controller continues to collect IEM values and to seek the maximum and minimum IEM values, at an IEM collection step 78. Based on the collected IEM values, the controller sets a threshold (THRESHOLD1) for use in identifying the optimal focal point, at a threshold setting step 80. For example, the threshold may be set to the IEM value measured a certain number (K) of frames after the maximum was reached, such as K=4 frames after the maximum. Focal scanning and IEM collection at step 80 continue until either the mechanism reaches the focus limit, at a limit checking step 82, or until a termination criterion is satisfied, at a scan termination step 84. Typically, this termination criterion requires that a sufficient number of frames (for example, ten frames) have elapsed beyond the frame with maximum IEM, and that the IEM value of the current frame is sufficiently far beneath the maximum value, for example, 25% below the maximum.

When the controller determines that it has reached the focal range limit at step 82 or satisfied the criterion of step 84, it again reverses the scan direction of the auto-focus mechanism, at a further scan reversal step 86. The controller now drives the auto-focus mechanism to scan back and forth over the range around the setting with maximum IEM until it converges on the optimal focus. As an initial step in this process, the controller sets a countdown timer to a number of frames that is equal to the current distance (in frames) from the maximum IEM value found in the scan of step 78, plus an overshoot of M1 additional frames, at a countdown setting step 88. Typically, M1 may be set to 10 frames, for example. The countdown timer is used, as explained below, in order to prevent excessive scanning back and forth, which may occur, for example, if the scene imaged by camera 22 has changed. Such a scene change may result in a change in IEM values as a function of the focal setting.

Following the scan direction reversal at step 86, the controller runs the auto-focus mechanism, at a convergent scanning step 90. The controller computes the IEM values of the captured images and seeks the point at which the IEM value of the current frame passes the threshold (THRESHOLD1), at a threshold checking step 94. The controller stops the search at this point, where the focal setting will likely be within a short distance of the optimal setting, at a process termination step 96.

Meanwhile, for each video frame that passes while scanning the auto-focus mechanism at step 90, the controller decrements the countdown timer that was set previously. If the threshold condition of step 94 is not satisfied, the controller terminates the current scan when the timer reaches zero, at a timer checking step 98. (As noted above, this sort of timeout may occur if the scene imaged by camera 22 has changed.) In this case, the controller again reverses the scan direction, at a final reversal step 100. For purposes of the reverse scan that is to follow, the controller finds the maximum IEM value of the scan performed at step 90, and sets a new threshold (THRESHOLD2) to the IEM value of the Kth frame following the maximum of this latter scan, at a new threshold setting step 92. The controller also resets the countdown timer to a final value M2, at a final timer setting step 102. M2 is typically set to a value greater than the overshoot value M1 that was set previously. M2 is chosen so that, if a significant maximum of the IEM value is not found in the subsequent scan, the auto-focus mechanism will be set at or near the focal setting for which the maximum IEM value was found previously.

After reversing the scan direction at step 100, the controller again runs the auto-focus mechanism, computes IEM values, and decrements the countdown timer, at a final scanning step 104. The scan terminates, at step 96, either when the IEM value of the current frame passes the threshold, at a final threshold checking step 106, or when the countdown reaches zero, at a final timer checking step 108. The focus of camera 22 should now be set at or near the optimal value for viewing the anatomical structures of interest to the user. If not, or if readjustment of the focal distance is needed subsequently for any reason, the user may again press control 34 or 35 in order to restart the auto-focus process.

Figure 4:
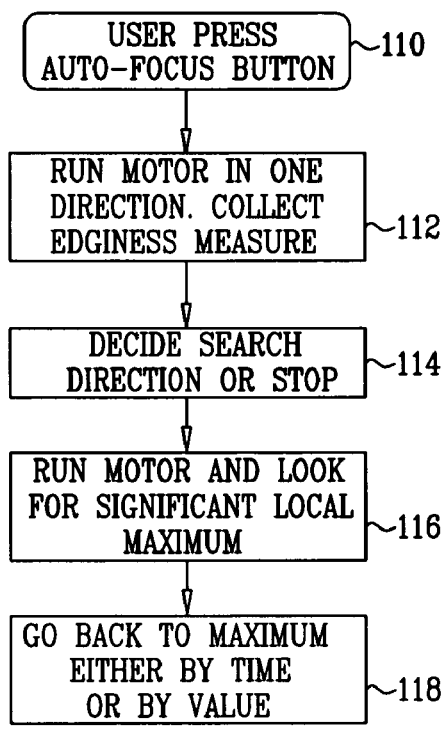
FIGS. 4 and 5 are flow charts that schematically illustrate methods for user-actuated auto-focus, in accordance with alternative embodiments of the inventive subject matter.

FIG. 4 is a flow chart that schematically illustrates a method for user-actuated auto-focus, in accordance with an alternative embodiment of the inventive subject matter. In this case (as well as in the embodiment of FIG. 5, described below), the user actuates auto-focus control 34 or 35 only to initiate the auto-focus process, at an initiation step 110. The controller does not rely on the user to release the control at or near the optimal focus, but rather scans the auto-focus mechanism autonomously, at a scanning step 112.

The controller computes and records edginess (IEM) values of the image frames during the scan, and then decides whether it has found a significant maximum value, at a decision step 114. If the scan passed a significant maximum, the controller reverses the scan direction and repeats the search, at a reverse scanning step 116, in a manner similar to that described above with reference to FIGS. 3A and 3B. Finally, the controller returns the auto-focus mechanism to the optimal setting, giving the maximal IEM value, either by time (countdown) or by IEM measurement, at a final setting step 118.

Figure 5:
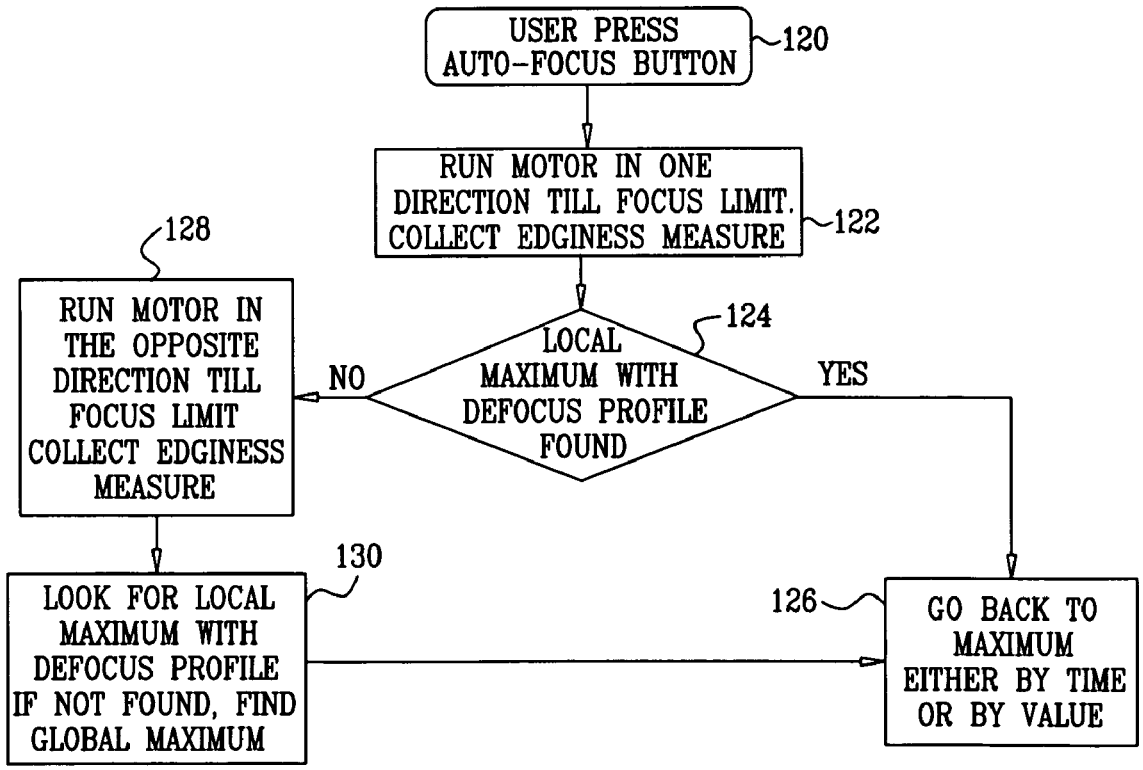

FIG. 5 is a flow chart that schematically illustrates a method for user-actuated auto-focus, in accordance with another alternative embodiment of the inventive subject matter. As in the embodiment of FIG. 4, the user in the present embodiment actuates the auto-focus control once, at an initiation step 120. The controller scans the auto-focus mechanism, typically all the way to the focus limit, at a scanning step 122. As in the preceding embodiments, the controller computes and collects the edginess measure of the image frames.

In the embodiment of FIG. 5, however, the controller searches not simply for a local maximum, but for a maximum with a defocus profile that has a shape similar to the expected shape for transition from focused to defocused optics, at a defocus assessment step 124. In other words, the controller evaluates the shape of the IEM curve as a function of focal distance (or equivalently, as a function of time or frame number). In particular, the controller tests the gradient of the curve against the expected range of gradients. The sort of test helps to ensure that the auto-focus process finds a true focal point, and does not converge to a local maximum in the IEM curve that is the result of artifacts, rather than optical focus. Such a test may also be incorporated in the method of FIGS. 2, 3A and 3B, as noted above.

If the controller finds a maximum in the IEM curve with the desired profile, it drives the auto-focus mechanism back to the setting that yielded this maximum, at a final setting step 126. Otherwise, the controller may repeat the scan of focal distance in the opposite direction, at a scan reversal step 128. The controller again computes and analyzes the IEM values to search for a local maximum with the desired profile, at a reverse assessment step 130. If the controller does not find a local maximum with the desired profile, it simply determines the global maximum of the IEM over the entire focal range, and then sets the focal distance at step 126 to give this global maximum vale.

In addition to the methods and systems disclosed herein, the inventive subject matter also contemplates a computer readable medium storing a set of instructions (i.e., software) executable by conventional computing devices and processors to perform the disclosed method steps. The inventive subject matter also contemplates methods of manufacture and assembly of systems apparatuses, and components disclosed herein.

It will be appreciated that the embodiments described above are cited by way of example, and that the inventive subject matter is not limited to what has been particularly shown and described hereinabove. Rather, the scope of the inventive subject matter includes both combinations and subcombinations of the various features described hereinabove, as well as variations and modifications thereof which would occur to persons skilled in the art upon reading the foregoing description and which are not disclosed in the prior art.

The invention claimed is:

1. A method for adjusting a video imaging system that includes an auto-focus mechanism, the method comprising:
   receiving an invoking input from a user of the video imaging system and invoking an auto-focus procedure, which is a procedure of adjusting a focal distance by scanning the auto-focus mechanism;
   after receiving the invoking input, adjusting the focal distance from a first focal distance to a second focal distance by scanning the auto-focus mechanism in a first direction from a first position of the auto-focus mechanism corresponding to the first focal distance to a second position of the auto-focus mechanism corresponding to the second focal distance;
   capturing a first sequence of images while scanning the auto-focus mechanism in the first direction;
   processing the images in the first sequence so as to compute a measure of focal quality with respect to each of the images in the first sequence;
   setting an optical focusing threshold value based on the computed measures of focal quality;
   after scanning the auto-focus mechanism in the first direction, reversing the scanning direction and adjusting the focal distance from the second focal distance toward the first focal distance by scanning the auto-focus mechanism in a second direction;
   capturing a second sequence of images while scanning in the second direction;
   processing the images in the second sequence so as to compute a measure of focal quality with respect to each of the images in the second sequence; and
   when the measure of focal quality which is computed from the images in the second sequence surpasses the threshold, terminating scanning in the second direction and setting, as an optimal focus position, a point at which the measure surpasses the threshold, wherein the act of invoking the auto-focus procedure comprises sensing a manipulation of a user control, wherein the method further comprises sensing an end to the manipulation of the user control, and, afterward, deciding whether to change a direction of the scanning based at least in part on the act of sensing the end to the manipulation of the user control.

2. The method according to claim 1, wherein the video imaging system comprises a camera, and wherein the user control comprises a button on the camera.

3. The method according to claim 1, wherein the end to the manipulation of the user control is indicative of an approximation by the user of the optimal focal distance.

4. The method according to claim 1, wherein processing the images comprises computing the measure of focal quality by evaluating edges in the images.

5. The method according to claim 1, wherein processing the images comprises computing the measure of focal quality over a plurality of windows within each of the images, and wherein analyzing the measure of the focal quality comprises selecting at least one of the windows so as to determine the optimal focal distance.

6. The method according to claim 1, wherein capturing the sequence of images comprises capturing the images of an anatomical structure inside a body of a subject using an endoscope.

7. The method according to claim 1, wherein the input is received while the video imaging system is directed to image a target used in a color balancing procedure.

8. The method according to claim 1, further comprising, after sensing the end to the manipulation of the user control, continuing to scan in the first direction until the auto-focus mechanism reaches the second position, and, subsequently, reversing the scanning direction.

9. The method according to claim 1, further comprising:
   after sensing the end to the manipulation of the user control, reversing the scanning direction, and, afterward, starting the scan in the first direction.

10. The method according to claim 1, wherein each captured image corresponds to a respective position of the auto-focus mechanism, the method further comprising:
    determining a maximum value of the measure of focal quality corresponding to the first sequence of images;
    capturing at least a selected number of images after capturing the image corresponding to the maximum value; and
    setting the second position corresponding to the last image of the at least selected number of images captured after capturing the image corresponding to the maximum value.

11. The method according to claim 10, wherein the act of capturing at least a selected number of images comprises capturing images at least until the measure of focal quality corresponding to the last captured image is less than a selected percentage of the maximum value.

12. The method according to claim 1, further comprising setting the second position of the auto-focus mechanism to a position at which the auto-focus mechanism reaches a limit of a focal range of the optics.

13. Apparatus for video imaging, comprising:
    an image sensor;
    imaging optics configured to form an image on the image sensor and comprising an auto-focus mechanism for adjusting a focal distance of the imaging optics;
    an auto-focus control configured to be operable by a user of the apparatus to generate an invoking input to invoke an auto-focus procedure, which is a procedure of adjusting the focal distance by scanning the auto-focus mechanism; and
    a controller configured to scan the auto-focus mechanism, after receiving the invoking input, in a first direction to adjust the focal distance from a first position of the auto-focus mechanism corresponding to a first focal distance to a second position of the auto-focus mechanism corresponding to a second focal distance, and to process a first sequence of images captured while scanning the auto-focus mechanism in the first direction so as to compute a measure of focal quality with respect to each of the images in the first sequence and to set an optical focus threshold value based on the computed measures of focal quality, wherein the controller is further configured to scan the auto-focus mechanism in a second, reverse direction to adjust the focal distance from the second position of the auto-focus mechanism after scanning in the first direction and to process a second sequence of images captured while scanning the auto-focus mechanism in the second direction so as to compute a measure of focal quality with respect to each of the images in the second sequence, and, when the measure of focal quality computed from the images in the second sequence surpasses the threshold, to terminate scanning the auto-focus mechanism in the second direction and to set a point at which the measure surpasses the threshold as an optimal focus position of the optics, wherein the auto-focus control is configured to generate the invoking input based on a manipulation of the user control; and the controller is configured to decide whether to change a direction of scanning of the auto-focus mechanism based at least in part on the sensed end to the manipulation of the user control.

14. The apparatus according to claim 13, further comprising a camera containing the image sensor, and wherein the auto-focus control comprises a button on the camera.

15. The apparatus according to claim 13, wherein the end to the manipulation of the user control is indicative of an approximation by the user of the optimal focal distance.

16. The apparatus according to claim 13, wherein the controller is configured to compute the measure of focal quality by evaluating edges in the images.

17. The apparatus according to claim 13, wherein the controller is configured to compute the measure of focal quality over a plurality of windows within each of the images, and to select at least one of the windows so as to determine the optimal focal distance.

18. The apparatus according to claim 13, and comprising an endoscope, wherein the image sensor is configured to capture the images of an anatomical structure inside a body of a subject using the endoscope.

19. The apparatus according to claim 13, wherein the controller is configured to receive the input while the video imaging system is directed to image a target used in a color balancing procedure.

20. The apparatus according to claim 13, wherein each captured image corresponds to a respective position of the auto-focus mechanism, wherein the controller is further configured to determine a maximum value of the measure of focal quality corresponding to the first sequence of images, to scan the auto-focus mechanism at least a selected number of positions past the position corresponding to the image having the maximum value of the measure of focal quality, and to set the second position of the auto-focus mechanism to the position corresponding to the at least a selected number of positions past the position corresponding to the image having the maximum value of the measure of focal quality.

21. The apparatus according to claim 20, wherein the controller is further configured to scan the auto-focus mechanism at least until the measure of focal quality of the last captured image is less than a selected percentage of the maximum value.

22. The apparatus according to claim 13, wherein the second position is a position at which the auto-focus mechanism reaches a limit of a focal range of the optics.

* * * * *